United States Patent [19]
Aneas

[11] Patent Number: 6,102,893
[45] Date of Patent: Aug. 15, 2000

[54] PREFILLED SAFETY SYRINGE

[75] Inventor: Antoine Aneas, Menetrol, France

[73] Assignee: Biodome, Issoire, France

[21] Appl. No.: 08/945,858

[22] PCT Filed: May 24, 1996

[86] PCT No.: PCT/FR96/00789

§ 371 Date: Nov. 7, 1997

§ 102(e) Date: Nov. 7, 1997

[87] PCT Pub. No.: WO96/37247

PCT Pub. Date: Nov. 28, 1996

[30] Foreign Application Priority Data

May 24, 1995 [FR] France .................................. 95 06415

[51] Int. Cl.⁷ .................................................. A61M 5/00
[52] U.S. Cl. ......................... 604/110; 604/111; 604/198; 604/263
[58] Field of Search ..................... 604/181, 187, 604/110, 192, 198, 263, 200, 218, 111, 199; 128/919

[56] References Cited

U.S. PATENT DOCUMENTS

| | | | |
|---|---|---|---|
| 4,085,737 | 4/1978 | Bordow | 604/263 |
| 4,248,246 | 2/1981 | Ikeda | 604/263 |
| 4,747,837 | 5/1988 | Hauck . | |
| 5,085,647 | 2/1992 | Henderson et al. . | |
| 5,226,894 | 7/1993 | Haber et al. | 604/198 |
| 5,267,972 | 12/1993 | Anderson . | |
| 5,342,309 | 8/1994 | Hausser | 604/110 |
| 5,366,447 | 11/1994 | Gurley . | |
| 5,372,590 | 12/1994 | Haber et al. | 604/192 |
| 5,540,666 | 7/1996 | Barta et al. | 604/192 |

FOREIGN PATENT DOCUMENTS

92/15351 9/1992 WIPO .
93/02728 2/1993 WIPO .

*Primary Examiner*—Ronald K. Stright, Jr.
*Attorney, Agent, or Firm*—Oliff & Berridge PLC

[57] ABSTRACT

A single-use disposable syringe device has a tubular body with a nose portion for receiving a hollow needle that communicates with an inner portion of the tubular body. The device also includes a sliding plunger provided opposite the nose portion inside the body, which is actuatable by the user at an upper end. The plunger is arranged in relation to the tubular body in a position where an innermost end defines an inner useful volume that is at least partially filled by a liquid medicinal substance. The device further includes a cap for protecting at least the nose portion and a protective sheath to be used after an injection. The cap is slidably mounted in a retracted position on and coaxial to the tubular body and has a length sufficient to completely cover the needle in an extended position. The cap is connected to the sheath or to the tubular body by a tamper-proof system.

5 Claims, 3 Drawing Sheets

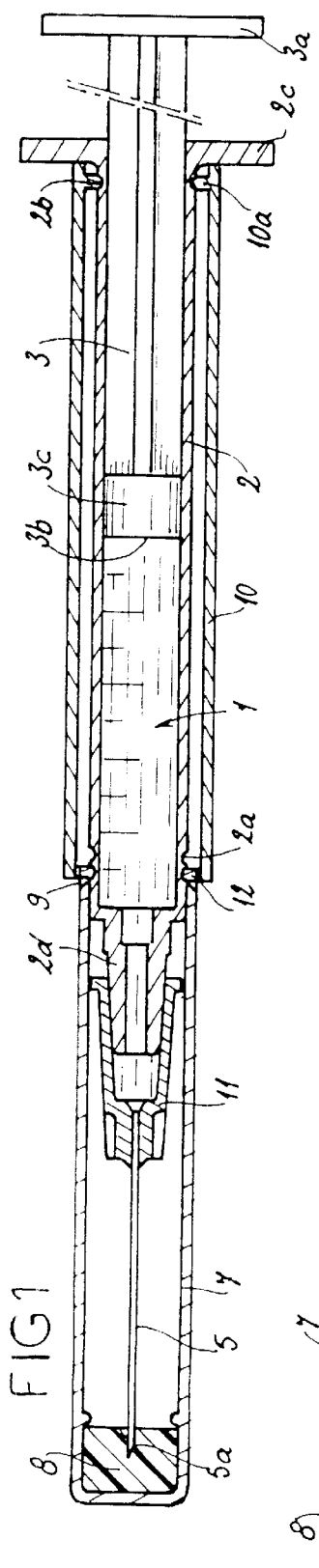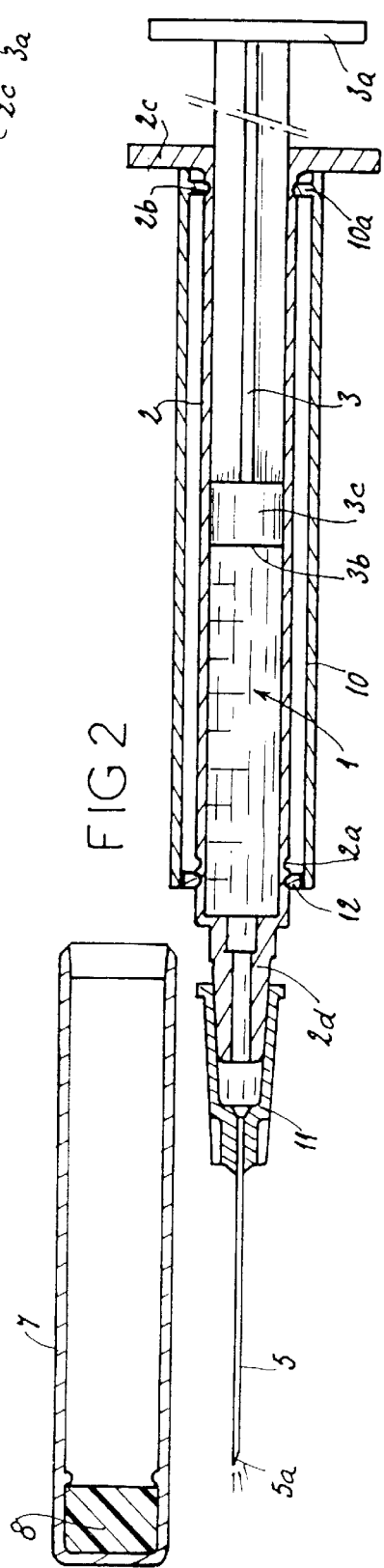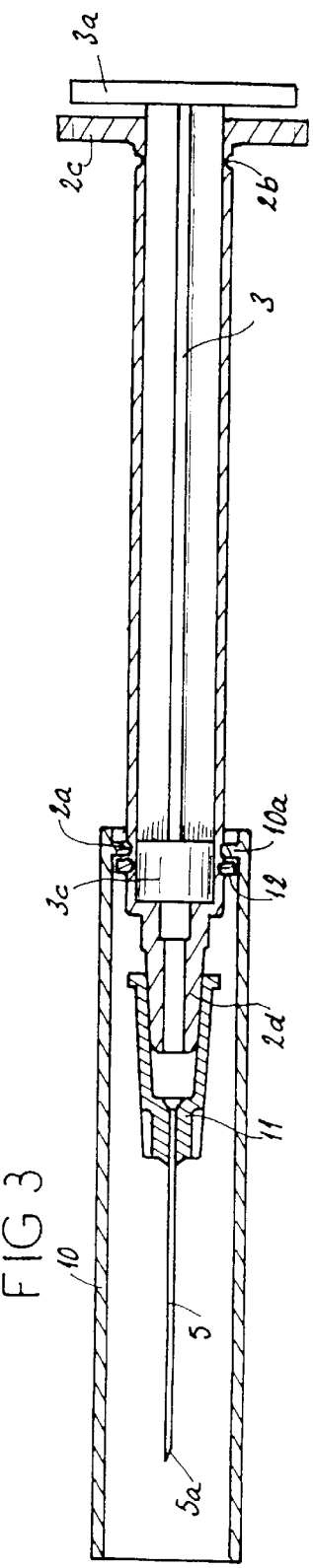

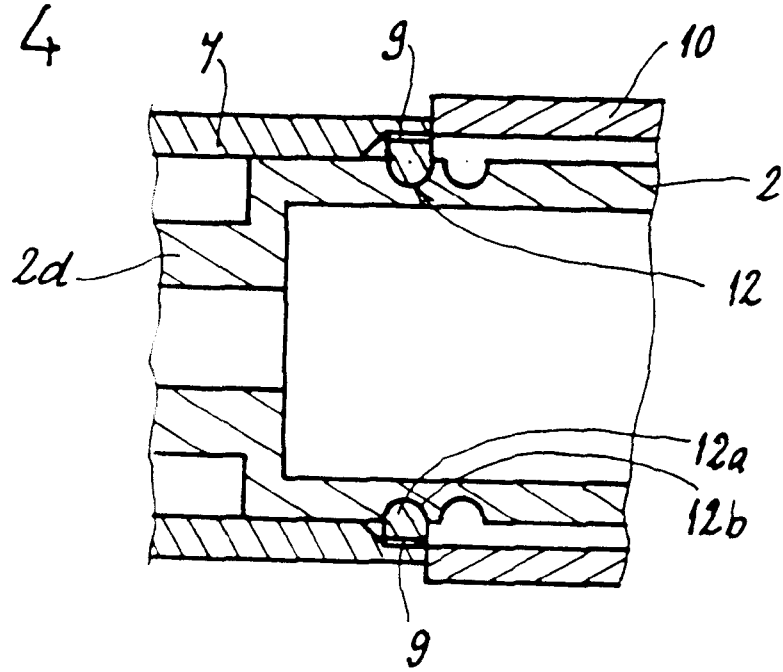
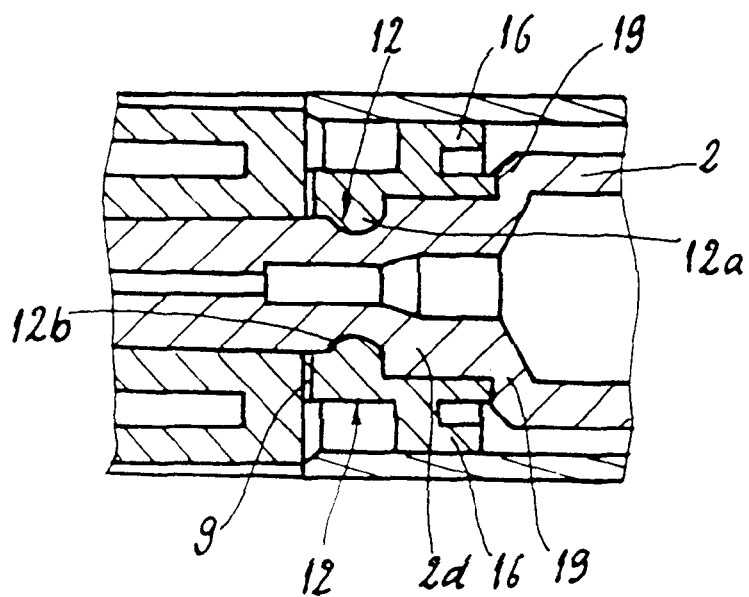

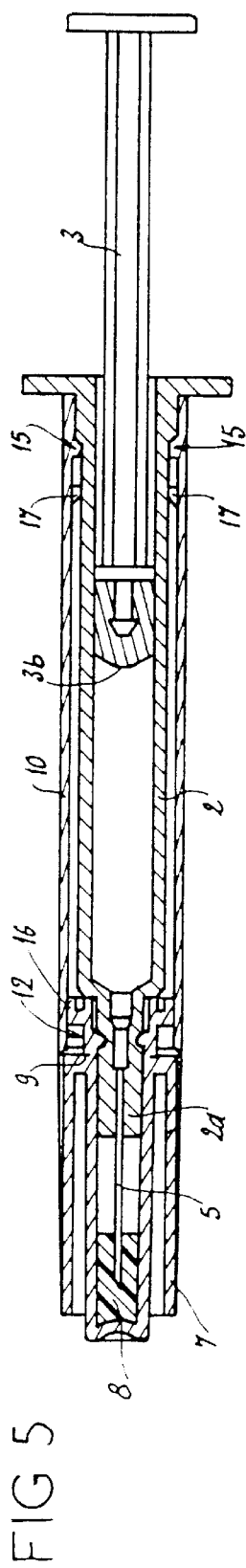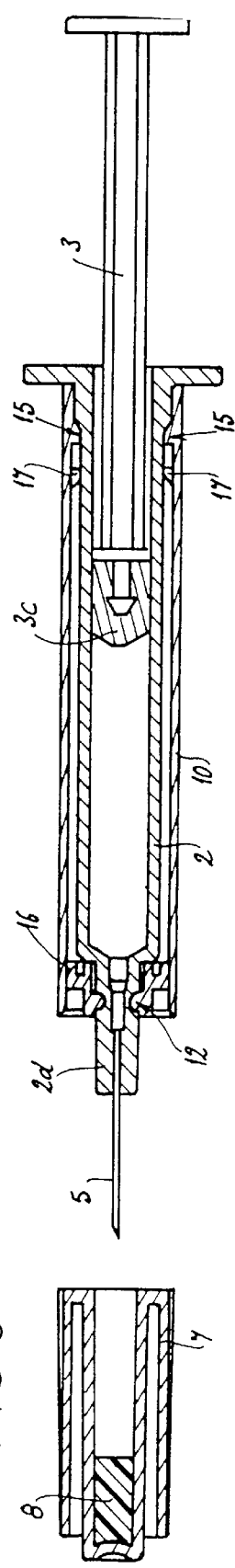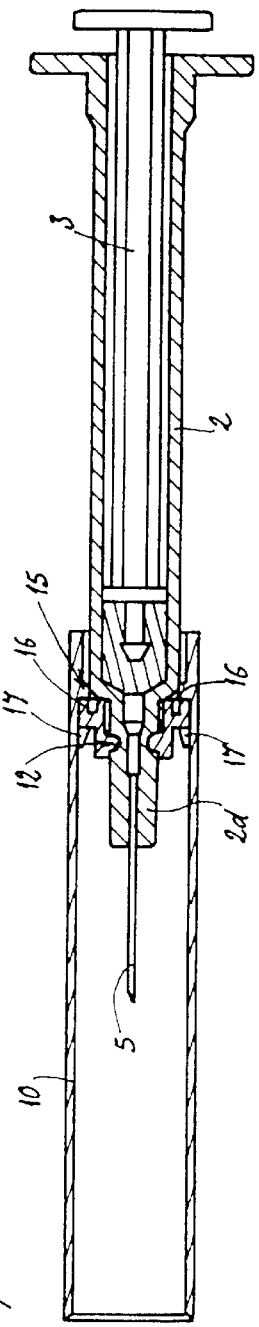

PREFILLED SAFETY SYRINGE

BACKGROUND OF THE INVENTION

This invention relates to a "vial-syringe" type medical device. In particular, the invention relates to a disposable prefilled syringe that is ready to be used.

Patent application No. WO-A-93/02728 describes such a conventional device having a tubular body, a nosepiece for a hollow needle, a sliding piston, a protective cover, a protective cap, and inviolability means. The tubular body may be transparent and contains the medicinal liquid that is to be injected in a patient. The nosepiece for the hollow needle communicates with the inside of the tubular body. A sliding piston is provided within the tubular body and is arranged in a predetermined position with respect to the tubular body opposite the nosepiece. The outside extremity of the sliding piston can be actuated by the user, while the inside extremity of the piston forms an internal space with the rest of the tubular body that is partially filled with a dose of the medicinal liquid. The protective cover is coaxial to and placed in a sliding manner on the tubular body and is of sufficient length to completely cover the needle in a protruding position after the injection is performed. The protective cap is positioned in a retractable manner on the front of the tubular body and protects at least the nosepiece of the tubular body. The inviolability means, in particular, is a low resistance, ring-shaped rip line.

A drawback of the above-described device is that it is possible to reuse the syringe by reinserting a new cartridge, which is detrimental in terms of safety and limits the field of application.

Pursuant to U.S. Pat. No. 4,747,837, a similar device is described but has a syringe that is not prefilled and the cap provided inside of the cover at the nosepiece of the body is held by means of friction rather than by inviolability means. This device is also provided with blocking means for the cover in its protruding position impeding any ulterior use. It is possible, however, to move the cover towards the front and to block it inadvertently, thus rendering the device unusable.

BRIEF SUMMARY OF THE INVENTION

The object of this invention is a device such as described above, incorporating inviolability means that concurrently ensures the imperviousness of the nozzle of the syringe against any contamination and protects the injection needle against any accidental pricking once the device has been used.

Another object of this invention is to solve the problems of the above-described devices by providing a single use disposable syringe device for medical use that assures the imperviousness of the device is not violated.

Furthermore, this invention also has the object of providing a device that compels the user to follow a certain procedure, thereby preventing any erroneous handling of the device because of the ergonomics of the device's construction.

In accordance with this invention, the cap is provided at its base with an annular retainer ring held in a permanent manner to the tubular body on the side of its nosepiece and attached to the rest of the cap by the inviolability means. The cap being designed with respect to the cover in such a manner that the cap blocks any sliding movement of the cover and remains in the retracted position while the cap is not separated from the tubular body. To achieve this, by way of example, the cap may be joined to the cover by the inviolability means. The retainer ring may also be fitted or arranged with respect to the cover so as to prevent the sliding movement of the cover in its protruding position.

Because of the design of this invention, it is impossible to change the sequence of the steps for its use and thereby prevents the reuse of the syringe.

Furthermore, blocking means for the cover in either the retracted and protruding positions can be provided between the tubular body and the cap.

In a preferred embodiment of this invention, the device comprises a hollow injection needle placed in the nosepiece of the tubular body. The cap can be of sufficient length to completely protect the needle prior to giving the injection and the interior of the cover opposite the tubular body can be provided with a stopper into which the injection end of the needle is located.

These and other objects of the invention will be described in or be apparent from the following description of preferred embodiments.

BRIEF DESCRIPTION OF THE DRAWINGS

The invention will be described in conjunction with the following drawings in which like reference numbers designate like elements and wherein:

FIG. 1 is a sectional view of a preferred embodiment of a device according to this invention in which the syringe is in a ready to be used state with a protective cap attached;

FIG. 2 is another sectional view of the device of FIG. 1 in which the syringe is prepared to give an injection to a patient as the cap is removed;

FIG. 3 is another sectional view of the device of FIGS. 1 and 2 after the injection has been given to a patient;

FIG. 4 is an enlarged view of the terminal extremity of the cover and the proximal extremity of the cap;

FIG. 5 is a sectional view of another preferred embodiment of a device rather than according to the invention in which the cover is mounted on the nosepiece of the body on the body;

FIG. 6 is a section view of the device of FIG. 5 after the removal of the cover, FIG. 7 is a sectional view of the device of FIGS. 5 and 6 after sliding and blocking the cap in its protruding position in order to prevent reuse of the device; and FIG. 8 is an enlarged view of a section of the device of FIG. 5.

DETAILED DESCRIPTION OF THE PREFERRED EMBODIMENTS

With exception, of course, of the hollow injection needle, it is possible to realize and obtain a device in accordance with invention by casting the various elements or components that comprise it. In accordance with FIGS. 1 to 3, the device 1 includes a tubular body 2 made of, for example, a transparent or translucent plastic material that is eventually provided with a graduation scale. The body 2 is prefilled to contain a medicinal liquid that is to be injected into a subject. Two perpendicular gripping wings 2c are provided on one extremity of the body 2 while a nosepiece 2d is provided on the other extremity, which serves as the assembly for a hollow injection needle 5. Two ring-shaped grooves 2a and 2b are provided on the outside of the body 2 on the side of the wings 2c and on the side of the nosepiece 2d, respectively, in order to interact with a cover 10.

A piston 3 having a plunger 3c that slides inside of the body 2 is actuated at an outside extremity 3a by the user. The piston 3 is held with respect to the tubular body 2 in a position in which an inside extremity 3b of the piston 3 forms an effective inside space that is filled with a dose of the medicinal liquid. The hollow injection needle 5 is provided at the extremity of the tubular body 2 opposite the piston 3 and is coaxially mounted with respect to the body 2 by an adapter 11, so that the needle 5 communicates with the interior of the body 2. A protective cap 7 for the needle 5 prior to giving the injection, as well as to obturate an open injection extremity 5a of the needle 5, encloses the needle 5 and is mounted in a detachable manner on the tubular body 2. The cap 7 is provided with a stopper 8, by way of example, made of rubber, into which the open injection extremity 5a of the injection needle 5 is placed. The stopper 8 is provided inside of the cap 7 on the side furthest from the tubular body 2.

A cover 10, for providing protection after the injection is given, is mounted in a sliding manner on and coaxial to the tubular body 2. The cover 10 is of sufficient length to cover the injection needle 5 in the protruding position. The cover 10 is positioned in a retractable manner on the tubular body 2 and is susceptible to being moved in a protruding position to the front of the body 2 in order to protect the injection needle 5 after the complete removal of the cap 7 and the use of the syringe.

The cover 10 includes at its base an annular retainer ring 12 screwed on in a permanent manner to the tubular body 2 on the extremity closest to the nosepiece 2d. The retainer ring 12 is linked to the cap 7 by inviolability means, such as, for example, plastic links that define a low resistance, ring-shaped rip line 9 that can be separated by the user. In a manner not shown, the retainer ring 12 and the body 2 are joined to each other by annular notching provided on the body 2 that correspond to notches on the inside of the retainer ring 12 so that it is possible to separate the cap 7 from the retainer ring 12 by merely unscrewing one from the other.

As shown in FIG. 4, the cap 7 is held with respect to the cover 10 in such a manner that the cap 7 blocks all movement of the cover 10, which remains in its retracted position, as long as the cap 7 is not separated from the tubular body 2. The cap 7 is held with respect to the cover 10 in order to block movement of the cover 10 from its protruding position, by jutting out from the front of the tubular body 2.

As shown in FIG. 3, because of a flange 10a, which is homologous to the grooves 2a and 2b of the tubular body 2, it is possible to keep the cover 10 in its retracted position due to the flange 10a engaging the groove 2b, and in its protruding position due to the flange 10a engaging the groove 2a.

The operation of the above-described device is discussed below. At the beginning, as shown in FIG. 1, the device is ready to be used, the cover 10 is retracted and the cap 7 is affixed to the body 2, thereby obturating the extremity 5a of the injection needle 5 with the stopper 8 and completely protecting the needle 5. By turning the cap 7 with respect to the retainer ring 12, the cap 7 separates from the body 2, thus uncovering the injection needle 5 which, in turn, allows a user to give a patient an injection by pushing the piston 3. After having given the injection, the cover 10 is slipped to its protruding position, which becomes permanent, so that the needle 5 is completely contained inside the cover 10 and is protected.

Another preferred embodiment of the invention, as shown in FIGS. 5 to 8, shall be described solely with respect to the differences to the embodiment shown in FIGS. 1 to 4. The reference numbers used shall be the same for the components common to both embodiments.

The device shown in FIGS. 5 to 8 is different in that the needle 5 is not mounted on an adapter 11, but rather is affixed directly to the nosepiece 2d by gluing or soldering, for example. As such, the needle communicates directly with the inside space of the tubular body 2. In this case, the cap 7 is sufficiently long enough to completely protect the needle 5 prior to giving the injection and, inside of said cap 7 opposite to the tubular body 2, a stopper 8 is provided into which is placed the extremity 5a of the needle 5. The cap 7 also comprises the retainer ring 12 that is firmly attached to the cap 7 and can be separated from the cap 7 when a rip force is applied to the low resistance ring-shaped line 9.

As best shown in FIG. 8, the retainer ring 12 is held to the nosepiece 2d of the tubular body 2 by means of an annular flange 12a that engages a corresponding annular groove 12b provided on the nosepiece 2d. The retainer ring 12 is furthermore provided with a projection or annular flange 16 that extends between the body 2 and the cover 10 towards the extremity of the piston 3 up to the shoulder 19 of the body 2. The cover 10 is provided with a ring-shaped projection 17 chamfered towards the front, so that when moved forward, the projection 17 of the cover 10 passes beyond the annular flange 16 of the retainer ring 12 and engages in front of the annular flange 16. Thus, any subsequent translatory movement is blocked by the annular flange constituting part of the blocking means 15 of the cover 10 in its retracted position, as described below.

The blocking means 15 of the cover 10 in its retracted position, provided between the tubular body 2 and the cover 10, includes, by way of example, a ring-shaped flange molded in the cover 10, chamfered on the side of the extremity of the piston 3, entering into elastic hold with the body 2 and preventing any movement of the body 2. After having given the injection, the cover 10 is pushed out and fixed in its protruding position, completely encasing the needle 5 by the ring-shaped flange that serves as blocking means 15 of the cover 10 in its protruding position and by the ring-shaped flange of the blocking means 15 that engages in the blocking space between the flange 16 and the shoulder 19 of the body 2.

What I claim is:

1. A ready-to-use prefilled syringe device for medical use by a user, comprising:

a hollow injection needle;

a tubular body having a nosepiece for housing the hollow injection needle such that the hollow injection needle communicates with an interior of the tubular body;

a piston that is slidable inside of the tubular body opposite to the nosepiece, the piston is actuatable from a back end of the tubular body at an outside extremity of the piston by the user and is held with respect to the tubular body in a predetermined position in which an inside extremity of the piston determines an effective inside space that is at least partially filled with a dose of a medicinal liquid;

a cover mounted coaxial to and in a sliding manner on the tubular body to provide protection after an injection, the cover is of a length sufficient to completely encase the hollow injection needle in a forward position protruding from a front end of the tubular body, the cover is held in a retracted position on the tubular body;

a protective cap having a first end and a second end, the first end is attached to the front end of the tubular body to protect the nosepiece of the tubular body;

inviolability means for preventing contamination having a low resistance, ring shaped rip line, the inviolability means is provided proximate to where the first end of the cap contacts the cover; and an annular retainer ring provided at the first end of the cap, the annular retainer ring being firmly affixed to the tubular body on the front end of the tubular body and is connected to the rest of the cap by the inviolability means, wherein the cap is held with respect to the cover in such a manner that the cap blocks any sliding movement of the cover, and the cover remains in the retracted position as long as the cap is not separated from the tubular body.

2. The device according to claim 1, wherein the retainer ring provided at the first end of the cap is arranged within an annular groove of the tubular body in such a manner that the retainer ring blocks the sliding movement of the cover in the protruding position and the retainer ring remains on the tubular body after the cap is removed.

3. The device according to claim 1, wherein between the tubular body and the cover are provided blocking means for blocking the movement of the cover in the retracted position, the blocking means comprising a groove provided at the back end of the tubular body and a first flange is provided at a locking end of the cover.

4. The device according to claim 1, wherein between the tubular body and the cover are provided blocking means for blocking the movement of the cover in protruding the position, the blocking means comprising a groove provided at the back end of the tubular body and a second flange is provided at the front end of the tubular body.

5. The device according to claim 1, wherein the hollow injection needle is fitted onto the nosepiece of the tubular body is of a length sufficient to completely protect the hollow injection needle before the injection and, inside of the cap opposite to the tubular body is a stopper into which an extremity of the hollow injection needle is placed.

\* \* \* \* \*